United States Patent [19]

Dal Moro et al.

[11] 4,452,630

[45] Jun. 5, 1984

[54] STABLE, HEAT-RESISTANT SOLUTIONS OF PESTICIDAL CARBAMATES

[75] Inventors: Anacleto Dal Moro; Franco Pinamonti, both of Milan, Italy

[73] Assignee: Montedison S.p.A., Milan, Italy

[21] Appl. No.: 322,202

[22] Filed: Nov. 17, 1981

Related U.S. Application Data

[63] Continuation-in-part of Ser. No. 172,296, Jul. 25, 1980, abandoned.

[30] Foreign Application Priority Data

Jul. 27, 1979 [IT] Italy ............................ 24733 A/79

[51] Int. Cl.³ .......................................... A01N 25/22
[52] U.S. Cl. .............................. 71/111; 71/DIG. 1; 71/113; 424/173; 424/300
[58] Field of Search ...................... 71/DIG. 1, 111; 424/300, 173

[56] References Cited

U.S. PATENT DOCUMENTS

| Re. 30,578 | 4/1981 | Metzger et al. | 71/111 X |
| 3,404,975 | 10/1968 | Wilson et al. | 71/100 |
| 4,163,662 | 8/1979 | Baker, Jr. | 71/DIG. 1 X |
| 4,213,776 | 7/1980 | Giilek et al. | 71/DIG. 1 X |

FOREIGN PATENT DOCUMENTS 1449768 9/1976 United Kingdom .

Primary Examiner—Catherine L. Mills

[57] ABSTRACT

Solutions and formulations of pesticidal carbamates having a high carbamate content and which are stable in the long run, as during storage, and can be exposed to temperatures of from 0° C. to 54° C. without undergoing alterations, i.e., without forming precipitates, etc., are disclosed. The stable solutions or formulations comprise, besides the carbamates, a solvent A which can be DMF, DMA or a mixture of the two and a solvent B which is any solvent, or mixture of solvents, mixable with solvent A, with the exception of alcohols, acids and aliphatic hydrocarbons.

9 Claims, No Drawings

STABLE, HEAT-RESISTANT SOLUTIONS OF PESTICIDAL CARBAMATES

This is a continuation-in-part of our application Ser. No. 172,296 filed July 25, 1980, and now abandoned.

BACKGROUND OF THE INVENTION

As is known, the pesticidal carbamates have the general formula

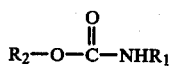

wherein:
$R_1$ is an alkyl, a phenyl, or an aryl; and
$R_2$ is an alkyl, a substituted alkyl, an aryl or a substituted aryl.

Some of the carbamates are endowed with herbicidal properties. These include, e.g., the following, the name for the same given in parenthesis being the name of the product according to ISO nomenclature:
methyl 3-m-tolyl-carbamoyloxyphenylcarbamate (Phenmedipham);
ethyl 3-phenylcarbamoyloxyphenylcarbamate (Desmedipham);
ethyl d(−)-1-(ethylcarbamoyl)-phenylcarbamate (Carbetamide).

Others of the carbamates are insecticides, including, e.g.:
methyl 1-naphthylcarbamate (Carbaryl);
methyl 2,3-dihydro-2,2-dimethylbenzofuran-7-ylcarbamate (Carbofuran);
methyl 2-isopropylphenyl-carbamate (Isoprocarb);
methyl-3,5-dimethyl-4-cyanomethylaminophenyl-carbamate (see Italian patent application No. 24,312 A/79).

Still others of the carbamates are fungicides, such as, for example, methyl benzimidazol-2-yl-carbamate (Carbendiazim).

These compounds are very little soluble in water, little soluble in aliphatic and aromatic hydrocarbons, rather soluble in alcohols and ketones. However, highly concentrated solutions cannot be obtained in the last-named solvents. Furthermore, at low temperatures, precipitates easily form, which lower the active product content thus making difficult the preparation of high-grade liquid concentrated formulated products.

The pesticide carbamates are soluble in dimethylformamide (DMF) or in dimethylacetamide (DMA). Such solvents, however, are expensive and, therefore, to prepare formulated products, less concentrated solutions in other, less expensive solvents are preferred.

THE PRESENT INVENTION

One object of this invention is to provide solutions, and formulations based on the solutions, having a high concentration of the pesticide carbamates and which are stable over long periods of time, remain unaltered during storage at low and high temperatures, and which are relatively inexpensive.

This and other objects which will be apparent to those skilled in the art from the description which follows are achieved by the invention in accordance with which it is found that surprisingly stable solutions of the pesticide carbamates can be obtained by mixing from 0.5 to 40% by weight of the carbamates with from 0.5–99% by weight of a solvent A and from 0.5 to 90% by weight of a solvent B.

Solvent A can be dimethylformamide, dimethylacetamide, or a mixture of the two.

Solvent B can be any solvent or mixture of solvents mixable with A, with the exception of alcohols, acids and aliphatic hydrocarbons.

Some examples of solvent B are:
chlorinated hydrocarbons such as, e.g., 1,2,3-trichloropropane;
aromatic hydrocarbons, such as toluene, xylene, ethylbenzene, styrene;
ketones, such as isophorone, methylethylketone, ethylamylketone, cyclohexanone, acetophenone;
cyclic ethers such as dioxane;
esters of aliphatic or aromatic organic acids, such as dioctylphthalate, methyl benzoate, benzyl acetate, 2-ethoxy ethylacetate, dimethylmaleate;
mixtures of aromatic hydrocarbons such as "Solvesso 200", (a commercial mixture based on dimethylethylbenzene and tetramethylbenzene having boiling point 227°–270° C.), or "Shellsol AB" (a commercial mixture based on dimethylethylbenzene and tetramethylbenzene having boiling point 185°–210° C.).

In general, with the exception of alcohols, acids and aliphatic hydrocarbons, B may be any solvent mixable with A, even if it is not, per se, a solvent for the carbamates.

The stability of the solutions is surprising and due to the fact that, unexpectedly, the presence of solvent B, in which compounds of the class of the carbamates are little, if at all, soluble, does not depress the solubility, which is similar to the result when solvent A is used alone.

Furthermore, while the carbamate solutions in pure solvent B generally alter (for example during storage at low temperatures they tend to let crystals separate), such phenomena do not occur in the mixtures of solvents A and B. In fact, the solutions so prepared are stable for 48 hours at 0° C.; moreover they remain stable at temperatures of 54° C. without undergoing any alterations, and are stable to storage for at least two years.

The solutions according to this invention can be additioned with ionic and non-ionic surfactants; they can be utilized for preparing aqueous emulsions, or, in the case of the insecticides, they can be used as such for ULV (ultra low volume) treatments, according to the known techniques concerning the formulations.

Surprisingly enough it may be demonstrated that the carbamates formulated following the invention show an enhanced biological activity in comparison with commercially available formulates and a lower toxicity.

The following examples are given to illustrate the invention in more detail and are not intended to be limiting.

EXAMPLE 1

40 g of Phenmedipham (herbicide) of formula:

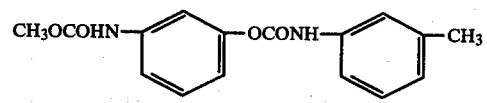

were dissolved in a mixture consisting of 30 g of DMF (dimethylformamide) and of 30 g of xylene by stirring for a few minutes and, if necessary, by heating, since the process is very endothermic. A limpid, complete solution was obtained, 50 g of which were subjected to a temperature of 54° C. for 14 days, while 50 g were subjected to a temperature of 0° for 48 hours.

At the conclusion of the heating and cooling period both solutions appeared unaltered. The analysis of two samples carried out directly on the solutions according to the TLC technique (thin layer chromatography) revealed that in both cases no meaningful degradation of the active substance had occurred.

EXAMPLE 2

40 g of M 10445 (Montedison insecticide; see Italian patent application No. 24,312 A/79), of formula:

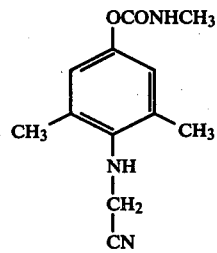

were dissolved in a mixture consisting of 30 g of DMF and of 30 g of xylol by stirring for a few minutes and, if necessary, by heating, since the process was very endothermic. A limpid, complete solution was obtained, 50 g of which were subjected to 54° C. for 14 days, while 50 g were subjected to 0° C. for 48 hours. At the conclusion of the heating and cooling period both solutions appeared unaltered. The analysis of the two samples carried out directly on the solutions according to the TLC (thin layer chromatography) technique revealed that no meaningful degradation of the active matter had occurred in either case.

EXAMPLE 3

30 g of Carbaryl (insecticide) of formula:

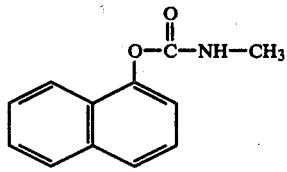

were dissolved in a mixture consisting of 40 g of DMF and 30 g of Solvesso 150, (a commercial mixture based on dimethylethyl benzene and tetramethyl benzene having boiling point 188°–210° C.), by stirring for a few minutes and heating, if necessary, since the process was very endothermic.

50 g of such solution were subjected to 54° C. for 14 days, while 50 g were subjected to 0° C. for 48 hours. After such periods both solutions appeared unaltered. The LGC (liquid gas chromatography) analysis of the two samples carried out directly on the two solutions revealed that no meaningful degradation had occurred in either case.

EXAMPLE 4

By operating according to the modalities of Examples 1, 2 and 3, the complete compositions comprising surfactants indicated in Table I were prepared. The indicated compositions appeared unaltered after the accelerated stability tests at 54° C. and at 0° C.

TABLE I

| Components | Compositions (g) | | | | |
|---|---|---|---|---|---|
| Phenmedipham | 40 | 40 | | | |
| M 10445 | | | 40 | 40 | |
| Carbaryl | | | | | 30 |
| DMF | 30 | 25 | 30 | 20 | 35 |
| Xylol | 20 | 10 | 20 | 10 | 15 |
| Cyclohexanone | | 15 | | 20 | 10 |
| Setrolene O(*) | | 3.5 | | 2 | |
| Rolfen 10 D(*) | 10 | 3.5 | 10 | 5 | 10 |
| Agrol Ca/L(*) | | 3.0 | | 3 | |

(*)Setrolene O = trademark of R. O. L. Montedison for sorbitanoleate polyoxyethylate (20 mols of ethylene oxide)
Rolfen 10 D = trademark of R. O. L. Montedison for acid nonylphenol polyoxyethylate phosphorylate having the formula:

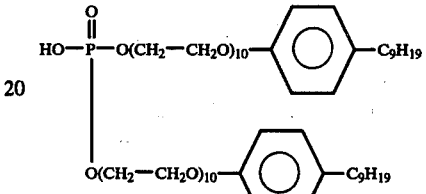

Argol Ca/L = trademark of R. O. L. Montedison for calcium dodecylbenzenesulphonate.

EXAMPLE 5

By operating according to the modalities of Examples 1, 2 and 3, the solutions indicated in Table II were prepared. The compositions indicated therein appeared unaltered after the accelerated stability tests at 54° C. and 0° C.

TABLE II

| Components | Compositions (g) | | | | | | | | |
|---|---|---|---|---|---|---|---|---|---|
| Phenmedipham | 40 | 40 | 40 | 40 | | | | | |
| M 10445 | | | | | 40 | 40 | 40 | | |
| Carbaryl | | | | | | | | 30 | 30 |
| DMF | 30 | 30 | 30 | | 25 | 25 | | 35 | |
| DMA | | | | 30 | | | 25 | | 30 |
| Shellsol AB | 30 | 10 | 15 | 15 | 35 | 20 | 20 | 10 | 10 |
| Acetophenone | | 20 | | | | | | 25 | |
| Cellosolve acetate | | | 15 | | | | | | |
| Amyl acetate | | | | 15 | | 15 | | | |
| Methylamyl-ketone | | | | | | | 15 | | 30 |

DMF = dimethylformamide
DMA = dimethylacetamide

EXAMPLE 6

Emulsifiable formulations of the herbicide Phenmedipham.

By operating according to Example 1 the compositions listed in Table III were prepared. The compositions indicated therein appeared unaltered after the accelerated stability tests at 54° C. and 0° C.

TABLE III

| | Compositions (g) | |
|---|---|---|
| Components | A | B |
| Phenmedipham | 16 | 30 |
| DMF | 15 | 25 |
| Xylene | 59 | 20 |
| Dioctylphthalate | — | 15 |
| Rolfen 10 D | 10 | 10 |

EXAMPLE 7

Comparison of the activity of a formulate of Phenmedipham according to the invention and a commercial formulate.

Infesting plants of beet cultivations were treated with the composition B of Phenmedipham described in Example 6 and with a commercial formulate ("Betanal" of Shering containing 15.9% of Phenmedipham and 10% of a tensioactive, the remainder being isophorone). The amount of active principle (100% Phenmedipham) was the same, in the tests with the composition B and with Betanal: 1.5 or 0.95 Kg/ha.

The test plants were kept in greenhouse at temperatures of 18°–28° C., with a photoperiod of 15 hours a day.

The results were detected by sight after 28 days from the treatment in a scale going from 0 (no activity) to 9 (full activity) and listed in the following Table IV.

TABLE IV

Comparison between the action of Bentanal (Shering's Phenmedipham formulate) and the action of formulate B of Table III on beet infesting plants.

| Formulate | Dose in 100% Phenmedipham Kg/ha | IPOMEA S. | VIGNA S. | STELLARIA M. | CONVOLVULUS S. | GERANIUM D. | SIDA S. | RUMEX A. | GALIUM A. | BEET |
|---|---|---|---|---|---|---|---|---|---|---|
| B (30% of Phenmedipham) | 0.95 | 9 | 9 | 9 | 9 | 2 | 8 | 9 | 7 | 0 |
|  | 1.5 | 9 | 9 | 9 | 9 | 2 | 8 | 9 | 8 | 0 |
| Betanal (15.9% of Phenmedipham) | 0.95 | 9 | 6 | 8 | 7 | 1 | 7 | 8 | 4 | 0 |
|  | 1.5 | 9 | 8 | 9 | 9 | 1 | 7 | 9 | 4 | 0 |

EXAMPLE 8

$LD_{50}$ of the Phenmedipham formulate in front of $LD_{50}$ of Betanal.

The acute oral toxicity of compositions A and B of Table III in male white rats genus Wistar (gastric sound) was proved to be respectively 11,000 mg/Kg and higher than 15,000 mg/Kg.

In the same conditions and on the same white rats the $LD_{50}$ of Betanal was proved to be 4,700 mg/Kg.

What we claim is:

1. A solution of the herbicide carbamate of formula

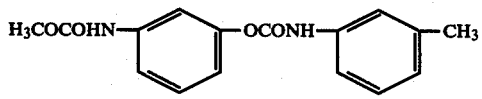 (I)

which solution is stable during storage at 54° C. for at least 14 days and at 0° C. for at least 48 hours, consisting of, in percent by weight:

| compound of formula (I) | 40 |
|---|---|
| dimethylformamide (DMF) | 30 |
| xylol | 30. |

2. A solution according to claim 1, and consisting of, in percent by weight:

| compound of formula (I) | 40 |
|---|---|
| DMF | 30 |
| xylol | 20 |
| nonylphenol-polyoxyethylate phosphorylate | 10. |

3. A solution according to claim 1, consisting of, in percent by weight:

| compound of formula (I) | 40 |
|---|---|
| DMF | 25 |
| xylol | 10 |
| cyclohexanone | 15 |
| sorbitan-oleate polyoxyethylate | 3.5 |
| nonylphenol polyoxyethylate phosphorylate | 3.5 |
| calcium dodecylbenzenesulphonate | 3.0. |

4. A solution according to claim 1, consisting of, in percent by weight:

| compound of formula (I) | 40 |
|---|---|
| DMF | 30 |
| mixture of alkyl-aromatic hydrocarbons having boiling point 185–210° C. | 30. |

5. A solution according to claim 1, consisting of, in percent by weight:

| compound of formula (I) | 40 |
|---|---|
| DMF | 30 |
| mixture of alkyl-aromatic hydrocarbons having boiling point 185–210° C. | 10 |
| acetophenone | 20. |

6. A solution according to claim 1, consisting of, in percent by weight:

| compound of formula (I) | 40 |
|---|---|
| DMF | 30 |
| mixture of alkyl-aromatic hydrocarbons having boiling point 185–210° C. | 15 |
| hydroxyethyl acetate | 15. |

7. A solution according to claim 1, consisting of, in percent by weight:

| compound of formula (I) | 40 |
|---|---|
| DMA | 30 |
| mixture of alkyl-aromatic hydrocarbons having boiling point 185-210° C. | 15 |
| amyl acetate | 15. |

8. A solution according to claim 1, consisting of, in percent by weight:

| compound of formula (I) | 16 |
|---|---|
| DMF | 15 |
| xylol | 59 |
| nonylphenol polyoxyethylate phosphorylate | 10. |

9. A solution according to claim 1, consisting of, in percent by weight:

| compound of formula (I) | 30 |
|---|---|
| DMF | 25 |
| xylol | 20 |
| dioctylphthalate | 15 |
| nonylphenol polyoxyethylate phosphorylate | 10. |

* * * * *